US006645921B2

(12) United States Patent
Gatto

(10) Patent No.: US 6,645,921 B2
(45) Date of Patent: Nov. 11, 2003

(54) MOLYBDENUM-CONTAINING LUBRICANT ADDITIVE COMPOSITIONS, AND PROCESSES FOR MAKING AND USING SAME

(75) Inventor: Vincent J. Gatto, Midlothian, VA (US)

(73) Assignee: Ethyl Corporation, Richmond, VA (US)

( * ) Notice: Subject to any disclaimer, the term of this patent is extended or adjusted under 35 U.S.C. 154(b) by 0 days.

(21) Appl. No.: 10/067,768

(22) Filed: Feb. 8, 2002

(65) Prior Publication Data

US 2003/0171226 A1 Sep. 11, 2003

(51) Int. Cl.[7] .......................... C10M 159/18
(52) U.S. Cl. .................. 508/362; 508/367; 554/38; 556/57
(58) Field of Search ................. 508/367, 362

(56) References Cited

U.S. PATENT DOCUMENTS

| | | | |
|---|---|---|---|
| 2,938,869 A | 5/1960 | Hugel | 508/261 |
| 3,121,059 A | 2/1964 | DeYoung | 252/42.7 |
| 4,164,473 A | 8/1979 | Coupland et al. | 252/32.7 |
| 4,259,195 A | 3/1981 | King et al. | 252/49.7 |
| 4,261,843 A | 4/1981 | King et al. | 252/49.7 |
| 4,266,945 A | 5/1981 | Karn | 44/68 |
| 4,692,256 A | 9/1987 | Umemura et al. | 252/32.7 |
| 4,765,918 A | 8/1988 | Love et al. | 252/46.4 |
| 4,889,647 A | 12/1989 | Rowan et al. | 252/42.7 |
| 5,137,647 A | 8/1992 | Karol | 252/33.6 |
| 5,143,633 A | 9/1992 | Gallo et al. | |
| 5,412,130 A | 5/1995 | Karol | 556/57 |
| 5,605,880 A | 2/1997 | Arai et al. | 508/379 |
| 5,840,672 A | 11/1998 | Gatto | 508/334 |
| 6,103,674 A | 8/2000 | Nalesnik et al. | 508/334 |
| 6,174,842 B1 | 1/2001 | Gatto et al. | 508/364 |
| RE37,363 E | 9/2001 | Gatto et al. | 508/364 |
| 6,509,303 B1 | 1/2003 | Gatto | |

FOREIGN PATENT DOCUMENTS

| | | | |
|---|---|---|---|
| EP | 0 546 357 B1 | 6/1993 | |
| EP | 1 136 496 A1 | 9/2001 | C07F/11/00 |
| EP | 1 136 497 A1 | 9/2001 | C07F/11/00 |
| GB | 2 053 268 A | 2/1981 | |
| WO | WO 95/07966 | 3/1995 | C10M/141/10 |
| WO | WO 00/55283 A1 | 9/2000 | |

*Primary Examiner*—Ellen M. McAvoy
(74) *Attorney, Agent, or Firm*—Dennis H. Rainear; Leah O. Robinson

(57) ABSTRACT

The invention relates to an improved process for producing organomolybdenum compositions with high molybdenum content that are highly useful as lubricant additives, in which the process involves reacting a fatty oil with a diamine, followed by reaction with a molybdenum source. The process of the present invention does not require a volatile organic solvent to promote molybdenum incorporation and produces an organomolybdenum composition having a high molybdenum content. In addition, the process can be conducted in the absence of sulfur and phosphorus-containing reactants.

44 Claims, No Drawings

`US 6,645,921 B2`

MOLYBDENUM-CONTAINING LUBRICANT ADDITIVE COMPOSITIONS, AND PROCESSES FOR MAKING AND USING SAME

TECHNICAL FIELD

The present invention relates to organomolybdenum compositions having high molybdenum content, which are useful as lubricant additives. The organomolybdenum compositions of the present invention are the reaction products of a fatty oil reacted with a diamine, followed by further reaction of the resulting intermediate with a molybdenum source to form the organomolybdenum product compositions, in which the process does not require a volatile organic solvent to promote and achieve high molybdenum incorporation in the additive product, nor does it require sulfur-containing or phosphorus-containing reactants nor post-reaction filtration removal for unreacted molybdenum source reactant.

BACKGROUND OF THE INVENTION

Lubricating oils used in the internal combustion engines of automobiles or trucks are subjected to a demanding environment during use. Among other adverse effects, this environment can lead to oxidative degradation of the oil. This oxidation of the oil is catalyzed by the presence of certain impurities in the oil, such as iron compounds. This oxidation also is promoted by the elevated temperatures to which the oil is subjected during use. The oxidation of lubrication oils during use is usually controlled in part by the use of antioxidant additives, which may extend the useful life of the oil, particularly by reducing or inhibiting unacceptable increases in the viscosity of the oil.

Various molybdenum compounds have been used and proposed as performance-enhancing additives for lubricant compositions. For instance, there are numerous examples in the patent literature which describe the use of molybdenum additives variously as antioxidants, deposit control additives, anti-wear additives and friction modifiers, in lubricant compositions. A partial list of such patent references includes, for example, U.S. Pat. Nos. 4,164,473, 5,840,672, 6,103,674, 6,174,842, and U.S. Reissued Pat. No. RE37,363 E, among others.

The preparation of organomolybdenum additives generally requires complicated reaction steps that add considerable cost to the manufacturing of these additives. Examples of some costly processing steps in this respect are as follows:

1. The use of volatile organic compound ("VOC") solvents, such as toluene, xylenes, 2-propanol, and dimethylformamide add considerable cost to the production of organomolybdenum compounds.
2. Low levels of molybdenum incorporation into the lubricant additive itself are achieved, which increases cost because higher concentrations of the resulting organomolybdenum product/additive must be used in the oil to deliver the required level of molybdenum to the crankcase package or finished oil. Ideally, it would be desirable to produce these organomolybdenum products/additives having molybdenum contents above 8 percent by weight, and preferably above 10 percent by weight.
3. Filtration is generally required to remove unreacted inorganic molybdenum. Unreacted molybdenum adds considerable cost to the production of organomolybdenum compounds because inorganic molybdenum is an expensive raw material.
4. Other costly processing steps associated with prior schemes for producing organomolybdenum components or lubricant additives include the need for acid or base neutralizations, the use of expensive catalysts or promoters, and water washes.

Examples of such prior processes for making organomolybdenum components or lubricant additives are reported, for example, in the patent literature as follows:

EP 1 136 496 discloses a product derived from methylaminopropylamine (R contains 1 carbon), which shows limited solubility in oil, while products containing 6 or more carbons in the R group have low molybdenum content (less than or equal to 8% undiluted).

EP 1 136 497 discloses molybdenum compounds derived from carboxylic acids and glycerides, which are relatively expensive.

U.S. Pat. No. 4,889,647 discloses molybdenum products that have relatively low molybdenum contents, for example 6 percent by weight, or lower.

U.S. Pat. No. 6,103,674 discloses molybdenum products that have low molybdenum contents, for example, 8 percent by weight or lower, and which contain sulfur.

Sulfur can be an undesirable component in engine oils. At high temperatures and under severe conditions, even the less aggressive forms of sulfur can cause corrosion, and in some cases elastomeric seal incompatibility (e.g., rubber hardening). Ideally, therefore, molybdenum compounds intended for use in lubricant engine oils should have minimal sulfur content.

U.S. Pat. No. 4,692,256 discloses a process for making an organomolybdenum compound that requires neutralization steps and water separations in order to isolate the organomolybdenum compound. When water is used as a promoter, as in U.S. Pat. No. 4,692,256, a filtration is required to remove unreacted molybdenum.

U.S. Pat. No. 5,137,647 discloses a sulfur and phosphorous-free organomolybdenum complex of organic amide, such as molybdenum containing compounds prepared from the reaction of fatty derivatives of 2-(2-aminoethyl)aminoethanol with a molybdenum source, in which the reaction temperature can be as high as 160° C. The sole example provided therein has a reaction temperature ranging from 130° C. to 140° C., and a filtration is carried out. Also, the reaction product is filtered, which adds an additional processing step.

U.S. Pat. No. 4,765,918 discloses molybdenum-containing compositions derived from fatty oils, amines, and a sulfur source.

U.S. Pat. No. 5,412,130 discloses molybdenum products derived from specially pre-treated fatty oils, e.g., treated by epoxidation followed by alkylation, that are reacted with molybdenum using a very specific fatty oil-derived catalyst. This special pre-treatment of the fatty oil adds considerable cost to the resulting product, making it impractical for use in lubricants.

The above problems suggest a previously unfulfilled need in the lubricant additive and composition industry and related technologies for oil soluble, sulfur-free molybdenum additives having high molybdenum content and low tendency to discolor finished oils without the need to use volatile solvents and without the need to remove non-reacted molybdenum. It has unexpectedly been found that the molybdenum additives of the present invention provide the above benefits to lubricating compositions without the attendant problems.

SUMMARY OF THE INVENTION

The present invention is directed to unique organomolybdenum compositions, which are especially useful as lubricant additives. To form the organomolybdenum compositions of this invention, a fatty oil, a diamine and a molybdenum source are combined in the absence of a volatile organic solvent yet effective to form a high organo molybdenum content reaction product. This reaction product obtained also does not have to be filtered to remove unreacted molybdenum source material.

In a more particular aspect, the present invention is directed to an organomolybdenum composition comprising the reaction product of a fatty oil reacted with an aliphatic diamine, followed by further reaction of the resulting intermediate reaction product with a molybdenum source in the absence of volatile organic solvent and without need for post-reaction filtering. In one preferred aspect, the first process step is performed neat, while in the second process step a small amount of water, but no volatile organic solvent is introduced or present during the molybdenum incorporation reaction, sufficient for the molybdenum source ingredient to go into solution such that reaction still proceeds well.

In one further aspect, the diamine reactant used is a monsubstituted amine having high hydrocarbon character, such as represented by the following general structure:

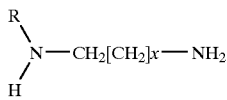

where x is 1 or 2, and R is a hydrocarbon-containing group containing at least about 6 carbon atoms. In one preferred aspect, the R group also contains oxygen, such as where R represents an alkyloxyalkylene group.

In another aspect, this invention provides a low cost process for producing sulfur- and phosphorus-free organomolybdenum compositions with high molybdenum content. In one aspect, the high molybdenum content of the reaction products of the process of the invention comprises from about 8 wt % to about 15 wt % molybdenum content (Mo). In addition, the process improvements achieved do not require the use and presence of a volatile organic solvent to achieve highly effective incorporation of molybdenum in the reaction product, and the resulting reaction product also does not require filtration to remove unreacted molybdenum source material such as molybdenum trioxide. The molybdenum-containing lubricant additives of the present invention are also very effective as antioxidants and deposit control additives in crankcase oils. Also, it has unexpectedly been found that preparation of the organomolybdenum compositions at reduced reaction temperatures according to another aspect of the present invention results in an improvement in the deposit control performance of the reaction product when used as an additive in engine oils. The molybdenum-containing lubricant additives of the present invention also are light colored complexes that are not prone to discoloration even when used at high concentrations in crankcase oils.

DETAILED DESCRIPTION OF THE INVENTION

In an embodiment of the present invention, the reaction scheme used to prepare the molybdenum additives includes a two step process. The first included step involves preparing an organic ligand comprised of an aminoamide/glycerol carboxylate mixture. This mixture is prepared by combining, mixing, contacting, or reacting (a) a fatty oil, vegetable oil, triglyceride or other glycerol ester of a higher fatty acid with (b) a mono-substituted alkylene diamine at an elevated temperature with heating. The second step involves carrying out the molybdenum incorporation.

Fatty Oils

Examples of preferred fatty or vegetable oils that may be used in the process of the present invention include groundnut oil, coconut oil, linseed oil, palm kernel oil, olive oil, cottonseed oil, grapeseed oil, corn oil, canola oil, palm oil, peanut oil, safflower seed oil, sesame seed oil, caster oil, rapeseed oil (low or high erucic acids), soyabean oil, sunflower oil, herring oil, sardine oil, lard, menhaden oil, hazel nut oil, walnut oil, and tallow, and mixtures thereof. These fatty or vegetable oils can include those compounds generally known as triglycerides, which have the general structure as shown below:

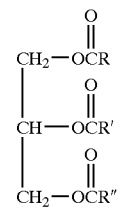

where R, R' and R" independently represent saturated or unsaturated aliphatic hydrocarbon groups having from about 8 to about 22 carbon atoms, and preferably are hydrocarbon chains having about 12 to about 22 carbon atoms. Mono- and diglycerides, either separately or in mixtures with one or more triglycerides, are also useful as fatty or vegetable oils in the present invention, in which the R, R', or R" groups present have the same above meaning.

The Diamine

In order to improve solubility of the organomolybdenum product in base oils and finished oils, it is important for the mono-substituted diamine to have a high hydrocarbon character. For example, the diamine can be represented by the following general structure:

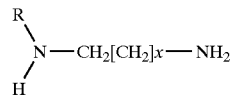

where x is 1 or 2, and R is a hydrocarbon-containing group containing a minimum of about 6 carbon atoms. R can be aliphatic or aromatic. R, in addition to the minimum of about 6 carbon atoms, may also contain oxygen, but preferably R does not include sulfur or additional nitrogen. It is preferred that R contains a minimum of 10 carbon atoms in order to further improve the organomolybdenum product solubility in base oil. The most preferred R contains an oxygen in addition to the carbons, such as where R is an alkyloxyalkylene group. Where R represents an alkyloxyalkylene group, R can be represented by the structure —$X_1$—O—$X_2$, where $X_1$ is an alkylene of 2, 3 or 4 carbons and preferably is propylene or ethylene, and $X_2$ is an alkyl moiety having 3 to 30 carbon atoms, more preferably an alkyl moiety having 7 to 20 carbon atoms, and where $X_2$ can be a straight or branched, saturated or partially unsaturated hydrocarbon chain. In diamines in which R is represented by such an alkyloxyalkylene group, both high incorporation of molybdenum, e.g., greater that 8.0 wt. % molybdenum incorporation, in to complexed product, as well as adequate oil-solubility are well imparted to the reaction product. The use of a diamine including an R group represented by —$X_1$—O—$X_2$ as defined herein in the reaction process makes it possible to maximize the level of molybdenum incorporation levels in the oil soluble reaction product while performing the process without the use of volatile organic processing solvents.

Examples of some mono-substituted diamines that may be used include phenylaminopropylamine, hexylaminopropylamine, benzylaminopropylamine, octylaminopropylamine, octylaminoethylamine, dodecylaminopropylamine, dodecylaminoethylamine, hexadecylaminopropylamine, hexadecylaminoethylamine, octadecylaminopropylamine, octadecylaminoethylamine, isopropyloxypropyl-1,3-diaminopropane, octyloxypropyl-1,3-diaminopropane, decyloxypropyl-1,3-diaminopropane, isodecyloxypropyl-1,3-diaminopropane, dodecyloxypropyl-1,3-diaminopropane, tetradecyloxypropyl-1,3-diaminopropane, isodecyloxypropyl-1,3-diaminopropane, isododecyloxypropyl-1,3-diaminopropane, isotridecyloxypropyl-1,3-diaminopropane. Mono-substituted diamines derived from fatty acids may also be used. Examples include N-coco alkyl-1,3-propanediamine (Duomeen C), N-tallow alkyl-1,3-propanediamine (Duomeen T), and N-oleyl-1,3-propanediamine (Duomeen O), all obtained from Akzo Nobel.

In order to produce an additive reaction product with a high molybdenum content, it is preferred to use a molar ratio of diamine to fatty oil in the first process step varying from about 1.50:1 to 3:1. A more preferred ratio is from about 1.75:1.0 to about 2.5:1.0.

The reaction between the fatty oil and mono-substituted diamine is carried out according to one embodiment at a temperature between about 100 and about 150° C. by combining the two materials and heating with mixing and under a nitrogen atmosphere. The preferred reaction temperature is between 110 and 130° C. Reaction times may vary from 1 hour to 6 hours. A reaction solvent, such as an organic reaction solvent, is not required.

As mentioned supra, the second included step of the process of the present invention involves carrying out the molybdenum incorporation, which is described in more detail below.

Molybdenum Source

A preferred molybdenum source is molybdenum trioxide. The use of molybdenum trioxide results in effective molybdenum incorporation into the organic ligand made by the aforementioned first process step, and it produces a reaction mass by the completion of the second step that does not require filtration if the reaction is performed properly according to guidance provided herein. Any purity grade of molybdenum trioxide may be used but high purity molybdenum trioxide is thought more likely to produce a product that does not require filtration.

Molybdenum Incorporation

A molybdenum source, such as molybdenum trioxide, and water are added to an aminoamide/glycerol carboxylate reaction mass obtained from the first process step and maintained at approximately 80° C. The molar ratio of molybdenum trioxide to diamine can vary from about 1:1.25 to about 1.25:1, and is preferably between 1:1.25 and 1:1 in order to maximize molybdenum content and at the same time reduce or eliminate the presence of unreacted molybdenum trioxide, which thus reduces or eliminates the need for filtration. The amount of water used in this second step should be an amount sufficient to incorporate all the molybdenum trioxide into the aminoamide intermediate and is generally equivalent to the amount of molybdenum trioxide used, but lower and higher levels of water may be used. After addition of the molybdenum trioxide and water the reaction components are slowly heated to reflux temperature with gradual removal of water. Water may be removed by vacuum distillation. The reaction may be carried out at temperatures ranging from 100° C. to 150° C., however, it has been found that temperatures below 140° C. are preferred for producing a molybdenum compound that is highly effective as a deposit control additive. The most preferred reaction temperature is below 130° C. The reaction generally requires 1 to 10 hours to remove all the water and this time will vary depending on the reaction temperature selected and the level of vacuum applied. During the water removal a diluent may be added to reduce the viscosity of the final product. However, a diluent is not required for the molybdenum incorporation. Preferred diluents include non-volatile diluents such as aromatic, paraffinic, and naphthenic process oils and base oils as well as synthetic oils and polyalphaolefins. A main advantage of this process is that a volatile organic solvent, such as toluene or xylenes, is not required in the second step for the water removal procedure or otherwise, nor are such organic solvents even used in the preferred embodiment.

At the end of the reaction period, the mixture is cooled and may be filtered to remove any unreacted molybdenum trioxide. Moreover, if the reaction is run optimally, filtration is not required, as tangible amounts of unreacted molybdenum trioxide will not be present. That is, the reaction step of molybdenum incorporation goes essentially to 100% completion. It is preferred to produce a reaction mass with complete molybdenum incorporation so that no post-reaction filtration is required to remove any unreacted molybdenum source material such as molybdenum trioxide. The product prepared by this process is a dark, amber wax or viscous liquid.

Further, when the molybdenum incorporation is performed at or below 130° C., improved deposit control in engine oils is achieved using the resulting additive product of the process of the invention.

The preferred combination of mono-substituted diamine, triglyceride, fatty oil or vegetable oil, and molybdenum trioxide, is that which produces a molybdenum content, undiluted with oil, greater than 8 wt. %, and preferably between 10 wt. % and 15 wt. %.

It is also an unexpected discovery that carrying out the molybdenum incorporation reactions at reduced temperatures improves the deposit control properties of the molybdenum product produced. This is demonstrated in the examples provided herein. It is therefore preferred to carry out the molybdenum incorporation reactions between 80 and 140° C., more preferably between 100 and 125° C.

The high molybdenum content organomolybdenum compositions of the present invention are useful to improve deposit control, antioxidant, antiwear, and/or friction modifying properties of lubricant oils, and like materials. The inclusion of the present molybdenum compounds generally removes the need for supplementary deposit control or antioxidants, antiwear additives and the like. However, a supplementary deposit control, antioxidant, and/or antiwear additive may be included in the finished oils including the molybdenum additives of the present invention that are less oxidatively stable or in oils that are subjected to unusually severe conditions. The treat rates of the molybdenum additives depend upon the desired finished lubricant properties, however, typically the additives are present in an amount so as to provide at least about 50, and preferably from about 50 to about 1000 ppm, of molybdenum to the finished product. The concentration of molybdenum in the lubricants according to the invention has no particular upper limit, however, for economic reasons a maximum level of about 1000 ppm is generally preferred although not required.

As an important aspect of the present invention, a process for making an organomolybdenum additive has been discovered which can be performed in the absence of volatile organic solvent without sacrificing the level of molybdenum incorporation or oil solubility of the reaction product. This process thus avoids the production and handling costs that otherwise would be associated with using such additional chemicals in performing the process. The language "absence of volatile organic solvent" means no volatile organic solvent is intentionally introduced or otherwise permitted to be present with the diamine, fatty oil and intermediate reaction product during the process of the present invention in amounts that might exceed trace amounts, that is, the amount of volatile organic solvent present, if any, during the process is less than 3.0 wt. % of the total reactor contents. From this standpoint, the process of the present invention consists essentially of the reaction product of fatty oil, diamine, and molybdenum source.

In addition, the organomolybdenum compositions of the present invention can be prepared without introducing sulfur or phosphorus. The organomolybdenum complex reaction products are substantially sulfur-free in the sense that the reaction itself introduces no sulfur into the reaction product, although some negligible trace levels of sulfur which are not part of the molybdenum product itself might be present due to impurities or catalysts left behind from the manufacturing process. Preferably, the amount of any sulfur in the organomolybdenum reaction product is less than 0.05 wt. %.

Sulfur can cause corrosion and elastomeric nitrile seal compatibility-hardening problems, among other things, while phosphorus can reduce automobile catalyst compatibility such as when used in crankcase oil formulations. The organomolybdenum compositions of the present invention can be formed free or at least substantially free of sulfur and phosphorus because no reactants including such materials are needed, nor used in the preferred embodiments.

When formulated into a lubricating oil, the organomolybdenum additives of the present invention optionally can be used in combination therein with one or more other additives including those typically used in lubrication oils. Typical additives used in lubrication oils, which optionally can be used in this respect, include detergents, corrosion inhibitors, rust inhibitors, additional antioxidants, dispersants, foam inhibitors, additional antiwear agents, additional friction modifiers, demulsifiers, VI improvers, pour point depressants, zinc dialkyldithiophopshates (ZDDP), and so forth. Examples of such optional supplemental additives are described, for example, in U.S. Pat. No. 5,840,672, which teachings are incorporated herein by reference.

The organomolybdenum compositions of the present invention are "oil soluble" in the sense that they are oil-soluble or capable of being solubilized under normal blending or use conditions into a lubrication oil or diluent for the concentrate.

The overall composition of a lubricating oil including the organomolybdenum additive such as described herein can vary significantly based on the customer and specific application. The additive of this invention can be employed in a variety of lubricating oil base stocks, such as derived from natural lubricating oils, synthetic lubricating oils or mixtures thereof. These oils include typical crankcase lubrication oils for spark-ignited and compression-ignited internal combustion engines, for example natural gas engines, automobile and truck engines, marine, and railroad diesel engines.

These oil base stocks can include, for example, hydrocracked base oils; mineral oils such as paraffinic, naphthenic or mixtures thereof; vegetable oils; petroleum oils, oils derived from coal shale; silicon-based oils; halosubstituted hydrocarbon oils; esters of dicarboxylic acids with alcohols; wax isomerate oils; polyalphaolefins, and mixtures thereof. In one preferred non-limiting embodiment, the base oils used in forming the lubricating compositions of the present invention are characterized by the presence of a high level of saturates and a very low level of sulfur, and include base oils referred to in the petroleum additive industry as Group II and Group III base oils. Further details on such base oils are described, for example, in U.S. Pat. No. 5,840,672, which teachings are incorporated herein by reference. In one non-limiting illustration, the base oils generally contain greater than or equal to 90% saturates, less than or equal to 0.03 weight percent sulfur and have a viscosity index of greater than or equal to about 80. The base oil typically has a viscosity generally of about 2 to about 15 cSt at 100° C.

In one non-limiting embodiment, the lubricant oil can be a formulated oil comprising between about 75 to about 95 weight percent (wt %) of a base oil of lubricating viscosity, between 0 and 30 wt % of a polymeric viscosity index improver, between about 5 and 15 wt. % of an additional additive package and typically a sufficient amount of molybdenum complex to provide at least about 50 ppm of molybdenum to the finished lubricant. The optional supplemental additives, for example, could be a supplemental detergent/inhibitor additive package and/or viscosity index improver. The present invention also encompasses the improved lubricating oil compositions, which contain the organomolybdenum additives of the present invention.

The organomolybdenum additives of the present invention can be used in lubricating oils such as crankcase oils for internal combustion engines, as well as gear lubricants, hydraulic fluids, automatic transmission fluids, turbine lubricants, engine fuels, compressor oils, lubricating greases, and so forth. The lubricating oil compositions of this invention can be made by adding the molybdenum compositions, and any supplemental additives, to an oil of lubricating viscosity. The method or order of component addition is not critical. Alternatively, the molybdenum compositions, along with any additional additives, can be added to the oil as a concentrate.

EXAMPLES

The following examples further illustrate aspects of the present invention but do not limit the present invention.

The attached examples demonstrate that organomolybdenum additives with undiluted molybdenum contents between 8.1 wt % and 11.4 wt % are easily produced using this process and inexpensive triglycerides as the fatty or vegetable oil reactant and starting material. It is possible using this process, and the right combination of diamine and vegetable oil, for example, to produce organomolybdenum additives with undiluted molybdenum contents as high as 15 wt %. The examples described herein also show that molybdenum incorporations performed at reduced temperature produce molybdenum additives with improved deposit control properties.

It has also been found that most of the organomolybdenum compounds produced in the examples described herein did not require filtration to remove unreacted molybdenum trioxide. Examination of filters after the filtration process showed no evidence of collected unreacted molybdenum trioxide or insolubles of any type in any appreciable quantities. Thus filtration is typically not required in the practice of the additive making process of the present invention.

The oil-soluble molybdenum-containing additives of the present invention may be used as antioxidants, deposit control additives, anti-wear additives, and/or friction modifiers. The table below summarizes treat rates and additive combinations for the various applications:

TABLE 1

| Application | Recommended Treat Range | Performance Boosting Additives | Oil Type |
|---|---|---|---|
| Antioxidant | 75–250 ppm Mo | Diphenylamines (0.05–1.0%) Sulfur Containing Additives (0.2–1.0%) Sulfurized Phenate Detergents (0.3–3.0%) ZDDP (0.5–1.2%) | Passenger Car and Medium Speed Diesel Oils |
| Anti-wear | 50–100 ppm Mo | ZDDP Sulfur Containing Additives | Passenger Car and Heavy Duty Diesel Oils |

TABLE 1-continued

| Application | Recommended Treat Range | Performance Boosting Additives | Oil Type |
|---|---|---|---|
| Deposit Control | 75–250 ppm Mo | Diphenylamines (0.05–1.0%) Sulfurized Phenate Detergents (0.2–3.0%) | Heavy Duty Diesel and Natural Gas Engine Oils |
| Friction Modifier | 250–1000 ppm Mo | Antioxidants (0.1–1.0%) Organic Friction Modifiers (0.3–1.0%) | Passenger Car Oils |

Example 1

Preparation of Sulfur-Free Organomolybdenum Additive (Sample No. 1)

A. Preparation of Amide Organic Ligand Intermediate Reaction Product

RBD Canola Oil (250.0 g, 0.277 mol) was added to a 500 mL resin kettle equipped with a reflux condenser, an addition funnel, a thermometer, a mechanical stirrer, and a heating mantle. Dry nitrogen was passed into the reactor through the addition funnel, and out of the reactor through the reflux condenser. The Canola Oil was heated to 80° C. and isodecyloxypropyl-1,3-diaminopropane (135.0 g, 0.458 mol) was added dropwise over 45 minutes. During the amine addition the reaction temperature was held at 80° C. The reaction mixture was then heated to 125° C. and held at that temperature, under nitrogen and with sufficient agitation, for 5½ hours. The reaction was cooled overnight.

B. Molybdenum Incorporation—Preparation of Organomolybdenum Derivative Complex Product The amide mixture intermediate reaction product, prepared as described above, was heated to 80° C. and the molybdenum trioxide (66.0 g, 0.459 mol) and water (35.0 g, 1.94 mol) are added. The reaction mixture rapidly rose to 95° C. The reaction mixture was then heated to reflux temperature and held at 111° C. for 30 minutes. Water was collected to a reaction temperature of 130° C. Shell E-C 100 N process oil (96.6 g) was then added. Vacuum was applied and the remaining water was removed at 130° C. over a 5 hour period. The resulting product was cooled to 100° C. and filtered using a pressure filtration apparatus. The product was isolated as an amber viscous oil. Weight of Product Collected=520 g. The physical and chemical properties of the organomolybdenum product are as follows: Viscosity @ 100° C.=71.93 cSt, Nitrogen Content=2.611 wt %, Molybdenum Content=8.298 wt %, Calculated Molybdenum Undiluted=10.1 wt %, TBN (ASTM D 2896)=32.3 mg KOH/g, IR Carbonyl Stretches=1738 $cm^{-1}$, 1639 $cm^{-1}$.

Preparation of Organomolybdenum Additive Sample Nos. 2–9

Additional samples of sulfur- and phosphorus-free organomolybdenum additives were prepared in a manner analogous to that described above, with modifications, reagents, reaction conditions, and properties as defined in the table below:

TABLE 2

| Additive Sample No. | 2 | 3 | 4 | 5 | 6 | 7 | 8 | 9 |
|---|---|---|---|---|---|---|---|---|
| Canola Oil (g) | 225.0 | 270.0 | 225.0 | 225.0 | 300.0 | 250.0 | — | 337.5 |
| Coconut Oil (g) | — | — | — | — | — | — | 190.0 | — |
| Diamine (g)[1] | — | — | 135.0 | 135.0 | 123.3 | 135.0 | 135.0 | 202.5 |
| Diamine (g)[2] | 115.0 | 114.0 | — | — | — | — | — | — |
| $MoO_3$ (g) | 50.0 | 49.2 | 51.0 | 65.0 | 59.3 | 71.5 | 66.0 | 98.0 |
| Water (g) | 25.0 | 25.0 | 25.0 | 35.0 | 30.0 | 35.0 | 35.0 | 52.5 |
| Process Oil (g) | 127.0 | 76.2 | None | 104.0 | None | 140.2 | 156.6 | 175.0 |
| Yield (g) | 497 | 492 | 377 | 499 | 456 | 545 | 530 | 774 |
| Mo Rx Temp. Range (° C.) | 80–120 | 80–120 | 80–120 | 80–125 | 80–130 | 80–140 | 80–140 | 80–140 |
| Visc. @ 100° C. (cSt) | 55.0 | 66.3 | 100.4 | 78.9 | 103.2 | 53.8 | 55.1 | 67.5 |
| Molybdenum (wt %) | 6.61 | 6.62 | 8.39 | 8.28 | 8.13 | 8.34 | 8.06 | 8.24 |
| Calc Mo Undiluted (wt %) | 8.8 | 7.8 | 8.4 | 10.4 | 8.1 | 11.0 | 11.4 | 10.6 |
| Nitrogen (wt %) | 2.40 | 2.44 | 3.40 | 2.66 | 2.65 | 2.38 | 2.64 | — |
| TBN (mg KOH/g) | 43.1 | 39.9 | 47.4 | 39.6 | 36.0 | 28.3 | 30.8 | 34.2 |
| IR carbonyl ($cm^{-1}$) | 1739, 1639 | 1739, 1640 | 1738, 1639 | 1739, 1640 | 1739, 1639 | 1739, 1639 | 1738, 1638 | 1738, 1638 |

[1]Isodecyloxypropyl-1,3-diaminopropane
[2]N-coco-1,3-diaminopropane

Preparation of Organomolybdenum Additive Sample No. 10

As an additional additive sample which was prepared, sample no. 10, 2-(2-aminoethylamino)ethanol was instead used as the diamine reactant. For this additional study, Step A, the preparation of the amide organic ligand was conducted in the same manner as described above except that 225.0 g (0.25 mol) of canola oil was used as the fatty oil reactant, and 47.7 g (0.458 mol) of 2-(2-aminoethylamino)ethanol was used as the diamine reactant. In step B, the molybdenum incorporation step, the amide mixture intermediate reaction product obtained from step A was heated to 80° C. and the molybdenum trioxide (65.0 g, 0.45 mol) and water (35.0 g, 1.94 mol) are added. The reaction mixture rapidly rose to 91° C. The reaction mixture was heated to reflux temperature to remove water. Excessive foaming was observed to occur at 102° C. Heating was continued and the foaming was observed to get considerably worse. Two drops of Dow Corning Fluid 20% was added to the reaction in an attempt to reduce the foaming. No reduction in foaming was observed. At this point the foaming was to the extent that the reaction mass started to climb out of the reactor, at which point the heating procedure was terminated. The heating mantle was removed while the reaction temperature was still above 100° C. Considerable foam was observed in the reaction product mass. Thus, the additive samples 1–9, which were performed without an organic reaction solvent and did not require any extraneous antifoaming agents, are preferable over additive sample 10.

Example 2

Evaluation of Organomolybdenum Additives in the Caterpillar Micro-Oxidation Test Organomolybdenum complexed product samples 1–9, as prepared in Example 1, were evaluated as additives in a modified version of the Caterpillar Micro-Oxidation Test (CMOT). Each additive was added to a separate amount of SAE grade 15W-40 fully formulated crankcase oil containing approximately 1000 ppm of phosphorus derived from ZDDP and 0.5 weight % of an alkylated diphenylamine antioxidant. This provided test Oils 1–9. A Comparison Oil was also tested in which the crankcase oil contained no molybdenum additive. The particular organomolybdenum complexed product among samples 1–9 used in each sample of base oil is indicated in Table 3. The additive treat levels were such that approximately 160 to 170 ppm of molybdenum was delivered to the respective finished Oils 1–9. For additives in the 8% molybdenum content range, this corresponds to 0.20 wt % of additive added to the lubricating oil formulation. For additives in the 6.5% content range, this corresponds to 0.25 wt % of additive content in the lubricating oil formulation.

The Micro-Oxidation Test is a commonly used technique for evaluating the deposit forming tendencies of a wide variety of passenger car and diesel lubricants as well as mineral and synthetic basestocks. The test measures the oxidative stability and deposit forming tendencies of lubricants under high temperature thin-film oxidation conditions. The ability to easily vary test conditions and the flexibility of presenting test results makes it a valuable research tool for screening a wide variety of lubricant products. In this test, a thin-film of finished oil is accurately weighed onto an indented low carbon steel sample holder sitting in a glass impinger tube. The sample, coupon and impinger tube assembly is then immersed in a high temperature bath. Dry air is passed, at a specific rate, through the impinger tube, over the oil sample, and out of the impinger tube to the atmosphere. At specific time intervals the carbon steel sample holders are removed from the high temperature bath, rinsed with solvent to remove any remaining oil, and oven dried. The solvent washes are filtered to collect any deposits that dislodge from the carbon steel holders. The sample holders and collected deposits are weighed to determine the amount of deposit formed at the sampling interval. Results are reported as the percent of oil sample forming deposit at a specific time interval. The induction time to deposit formation can also be determined by calculating the intercept between the baseline formed where minimal deposits are seen, and the slope formed where a rapid rise in deposit formation is seen. Longer induction times correspond to improved deposit control. Another parameter of value in this test is the Performance Index (PI). The Performance Index represents the reduction in deposit formation of the additized finished oil over the entire sampling range of testing versus the baseline finished oil over the same sampling range. The formula for calculating PI is as follows:

$$PI = [((\text{area of baseline oil}/\text{area of additized oil}) - 1) \times 100].$$

A larger Performance Index (PI) corresponds to improved deposit control.

The test conditions used to evaluate the test oils 1–9 are as follows: gas=dry air, flow=20 cc/minute, temperature=230° C., sampling interval=50, 60, 70, 80, 90, 100, 110, 120 minutes, sample size=approximately 20 microL accurately weighed.

The deposit control results, as reported in percent deposits (wt %), for the tested oils containing the respective organomolybdenum compounds are shown in the table below:

TABLE 3

| Test Oil | Comp. Oil 1 | Oil 1 | Oil 2 | Oil 3 | Oil 4 | Oil 5 | Oil 6 | Oil 7 | Oil 8 | Oil 9 |
|---|---|---|---|---|---|---|---|---|---|---|
| Additive Sample No. | No Mo Additive | 2 | 3 | 1 | 4 | 5 | 6 | 7 | 8 | 9 |
| Time (min) | wt. % dep's | wt. % dep's | wt. % dep's | wt. % dep's | wt. % dep's | wt. % dep's | wt. % dep's | wt. % dep's | wt. % dep's | wt. % dep's |
| Percent Deposits (wt. % dep's) as a Function of Time | | | | | | | | | | |
| 50 | 4.4 | 1.4 | 1.9 | 1.1 | 2.1 | 4.2 | 2.0 | 2.6 | 1.3 | 3.2, 3.1 |
| 60 | 5.4 | 2.2 | 2.0 | 4.6 | 4.2 | 4.2 | 2.1 | 3.5 | 1.4 | 3.4, 3.2 |
| 70 | 15.3 | 2.3 | 2.4 | 6.2 | 4.7 | 4.3 | 2.2 | 3.5 | 1.9 | 3.4, 3.4 |
| 80 | 16.4 | 2.8 | 2.6 | 6.3 | 4.8 | 4.3 | 2.6 | 3.9 | 2.1 | 3.7, 4.1 |
| 90 | 19.9 | 2.9 | 3.9 | 6.6 | 4.8 | 7.8 | 6.1 | 4.4 | 6.4 | 8.9, 8.3 |
| 100 | 21.4 | 2.9 | 10.8 | 9.0 | 4.8 | 10.3 | 11.0 | 17.1 | 8.8 | 18.2, 19.5 |
| 110 | 30.5 | 6.6 | 11.2 | 14.2 | 4.8 | 8.8 | 19.9 | 15.7 | 12.7 | 21.6, 16.1 |
| 120 | 28.8 | 6.2 | 11.0 | 20.0 | 14.7 | 8.8 | 19.1 | 15.7 | 20.5 | 22.5, 15.6 |
| Onset to Deposit Formation | | | | | | | | | | |
| Min | 53 | 101 | 89 | 96 | 111 | 80 | 82 | 90 | 82 | 81, 80 |
| Performance Index (PI) = [((area No Mo/area plus Mo) − 1) × 100] | | | | | | | | | | |
| PI | | 421 | 210 | 109 | 216 | 170 | 119 | 114 | 158 | 67, 94 |

Thus, the molybdenum-containing compositions of the present invention demonstrate a clear trend toward improvement in deposit control in an engine. Also shown is a significant reduction in deposits when the molybdenum additives are prepared at lower reaction temperatures.

Example 3

Evaluation of Organomolybdenum Additives for Oil Coloration

A color and visual solubility were determined for the molybdenum complexed compounds of sample nos. 1–8, as described in Example 1, using a paraffinic process oil diluent (PO#5). The color method was ASTM D 1500. Color results are reported to the nearest one-half unit match on the D1500 color scale. The treat levels were 1 wt. % for each tested sample, in which the treat level is based upon the amount (weight percent) of the molybdenum compound added to the process oil, not the amount of molybdenum delivered to the process oil. An additional sample, sample no. 11, was prepared and tested in a similar manner for solubility, and color in which the organomolybdenum complexed product used was prepared in the manner described for additive Sample M6 as described in European published patent application EP 1 136 496 A1. The M6 additive involves the reaction product of 2-(2-aminoethylamino)ethanol and canola oil in which an organic reaction solvent is used during molybdenum incorporation.

The color and oil solubility results observed for these tests are summarized below in Table 4. The higher the D1500 color value reported, the greater the darkening of the process oil that has occurred on account of the addition of the organomolybdenum additive.

TABLE 4

| Additive Sample No. | 1 | 2 | 3 | 4 | 5 | 6 | 7 | 8 | 11 |
|---|---|---|---|---|---|---|---|---|---|
| D1500 Color in PO#5 | 1.5 | 1.0 | 1.0 | 1.5 | 1.5 | 1.5 | 2.5 | N/A | 3.5 |
| Solubility in PO#5 | yes | yes | yes | yes | yes | yes | yes | no | yes |

From an examination of the results in Table 4, it is apparent that that the molybdenum compounds made with diamine reactant in which the R group substituent, with reference to the diamine chemical structure described above herein, was an alkyloxyalkylene group, such as in samples 1–7, had the optimal color properties. It also is apparent that the molybdenum compounds made with canola oil reactant (i.e., in which the R, R' and R" hydrocarbon chains therein are in the range of $C_{12}$ to $C_{22}$, with reference to the fatty oil chemical structure described above herein) had excellent oil solubility.

Other embodiments of the present invention will be apparent to those skilled in the art from consideration of the specification and practice of the invention disclosed herein. It is intended that the specification and examples be considered as exemplary only, with a true scope and spirit of the invention being indicated by the following claims. It is to be understood that both the foregoing general description and the following detailed description are exemplary and explanatory only and are intended to provide further explanation of the present invention, as claimed. This invention is susceptible to considerable variation in its practice. Accordingly, this invention is not limited to the specific exemplifications set forth hereinabove. Rather, this invention is within the spirit and scope of the appended claims, including the equivalents thereof available as a matter of law.

The patentee does not intend to dedicate any disclosed embodiments to the public, and to the extent any disclosed modifications or alterations may not literally fall within the scope of the claims, they are considered to be part of the invention under the doctrine of equivalents.

What is claimed is:

1. A composition comprising the reaction product of a fatty oil, a diamine, and a molybdenum source in which the reaction product is formed in the absence of carbon disulfide and volatile organic solvent.

2. The composition according to claim 1, wherein molybdenum source is molybdeum trioxide.

3. The composition according to claim 1, wherein the fatty oil is selected from a vegetable oil and a triglyceride, or a mixture thereof.

4. The composition according to claim 1, wherein the fatty oil is selected from groundnut oil, coconut oil, linseed oil, palm kernel oil, olive oil, cottonseed oil, grapeseed oil, corn oil, canola oil, palm oil, peanut oil, safflower seed oil, sesame seed oil, caster oil, rapeseed oil, soyabean oil, sunflower oil, herring oil, sardine oil, lard, menhaden oil, hazel nut oil, walnut oil, and tallow, and mixtures thereof.

5. The composition according to claim 1, wherein the fatty oil is a triglyceride having the formula:

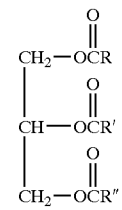

wherein R, R', and R" each independently represents a saturated or unsaturated hydrocarbon chain group having about 8 to about 22 carbon atoms.

6. The composition according to claim 1, wherein the vegetable oil comprises canola oil.

7. The composition according to claim 1, wherein the diamine is selected from phenylaminopropylamine, hexylaminopropylamine, benzylaminopropylamine, octylaminopropylamine, octylaminoethylamine, dodecylaminopropylamine, dodecylaminoethylamine, hexadecylaminopropylamine, hexadecylaminoethylamine, octadecylaminopropylamine, octadecylaminoethylamine, isopropyloxypropyl-1,3-diaminopropane, octyloxypropyl-1, 3-diaminopropane, decyloxypropyl-1,3-diaminopropane, dodecyloxypropyl-1,3-diaminopropane, tetradecyloxypropyl-1,3-diaminopropane, isodecyloxypropyl-1,3-diaminopropane, isododecyloxypropyl-1,3-diaminopropane, isotridecyloxypropyl-1,3-diaminopropane, mono-substituted diamines derived from fatty acids, N-coco alkyl-1,3-propanediamine, N-tallow alkyl-1,3-propanediamine, and N-oleyl-1,3-propanediamine, and mixtures thereof.

8. The composition according to claim 1, wherein the diamine has the chemical structure

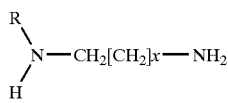

wherein x is 1 or 2 and R is an alkyl or alkyloxyalkylene group.

9. The composition according to claim 8, wherein R has at least 10 carbon atoms.

10. The composition according to claim 8, wherein R further contains oxygen and is devoid of sulfur and nitrogen.

11. The composition according to claim 8, wherein R represents an alkyloxyalkylene group.

12. The composition according to claim 8, wherein R is represented by the structure —$X_1$—O—$X_2$, wherein $X_1$ is an alkylene of 2, 3 or 4 carbons, and $X_2$ is an alkyl moiety having 3 to 30 carbon atoms, and where $X_2$ can be a straight or branched, saturated or partially unsaturated hydrocarbon chain.

13. The composition according to claim 1, wherein the molar ratio of diamine to fatty oil is from about 1.5:1 to about 3:1.

14. The composition according to claim 1, wherein the molar ratio of molybdenum to diamine is from about 1:1.25 to about 1.25:1.

15. The composition according to claim 1 containing less than 0.05 weight percent sulfur.

16. The composition according to claim 1 having a molybdenum content of from about 8.1 wt % to about 15 wt %.

17. The composition according to claim 1 having a molybdenum content of from 10.0 wt % to 15.0 wt %.

18. An oil soluble composition comprising the reaction product of a fatty oil, a diamine, and a molybdenum source, wherein the diamine has the chemical structure:

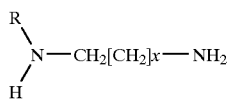

wherein x is 1 or 2, and R is an alkyloxyalkylene group represented by —$X_1$—O—$X_2$, wherein $X_1$ is an alkylene of 2, 3 or 4 carbons, and $X_2$ is an alkyl moiety having 3 to 30 carbon atoms, and wherein the fatty oil comprises a triglyceride having fatty acid moieties, and said fatty acid moieties comprise $C_{12}$ to $C_{22}$ hydrocarbon chains, and wherein the oil soluble composition includes a molybdenum content of from about 8.1 wt % to about 15 wt %.

19. The oil soluble composition according to claim 18, wherein the molybdenum source comprises molybdenum trioxide.

20. The oil soluble composition according to claim 18, wherein x is 2, $X_1$ is 2, 3 or 4, and $X_2$ is an alkyl group having 3 to 20 carbon atoms.

21. The oil soluble composition according to claim 18, wherein the molar ratio of diamine to fatty oil is from about 1.5:1 to about 3:1.

22. A composition according to claim 1, said composition diluted with a process, mineral or synthetic oil.

23. A lubricating oil composition comprising a major amount of an oil of lubricating viscosity, and a minor amount of a composition according to claim 1 present in an amount sufficient to provide at least 50 ppm of molybdenum in the lubricating oil composition.

24. A composition according to claim 18, said composition diluted with a process, mineral or synthetic oil.

25. A process for preparing a molybdenum-containing composition, comprising reacting a fatty oil, a diamine, and a molybdenum source, in the absence of carbon disulfide and volatile organic solvent.

26. The process according to claim 25, which comprises:
(a) reacting a fatty oil with a diamine to form an intermediate reaction mixture, and
(b) adding a molybdenum source to thus obtained intermediate reaction mixture, wherein (a) and (b) are performed without introducing volatile organic solvent.

27. The process according to claim 26, wherein the intermediate reaction mixture comprises an aminoamide/glycerol carboxylate mixture prepared by combining a glycerol ester of a fatty acid selected from a fatty oil, vegetable oil, triglyceride, or a mixture thereof, with a mono-substituted alkylene diamine.

28. The process according to claim 27, further comprising incorporating molybdenum into the intermediate reaction mixture by combining a molybdenum source with the aminoamide/glycerol carboxylate mixture.

29. The process according to claim 27, further comprising combining and heating the glycerol ester of a fatty acid and the mono-substituted alkylene diamine with mixing at a temperature between about 100 degrees Celsius and about 150 degrees Celsius.

30. The process according to claim 27, wherein the molybdenum source is molybdenum trioxide.

31. The process according to claim 27, wherein the molybdenum source and water are combined with the aminoamide/glycerol carboxylate mixture for a time and at a temperature sufficient to produce a molybdenum-containing reaction product.

32. The process according to claim 31, wherein the time is from 1 to about 10 hours and the temperature is from about 100 degrees Celsius to about 150 degrees Celsius.

33. A composition produced by the process of claim 26.

34. The composition of claim 33, wherein the composition contains less than 0.05 wt % sulfur.

35. The composition of claim 33, wherein the composition comprises from 10.0 wt % to 15.0 wt % molybdenum.

36. The composition of claim 33, wherein the composition comprises between 8.1 wt % and 11.4 wt % molybdenum.

37. A process of lubricating a crankcase comprising adding the composition of claim 1 to a crankcase.

38. A crankcase lubricated with a composition of claim 1.

39. An organomolybdenum composition comprising the reaction products of (i) at least one fatty oil; (ii) at least one mono-alkylated alkylene diamine; and (iii) a molybdenum source, wherein the organomolybdenum composition includes a molybdenum content of from about 8.1 wt % to about 15 wt %.

40. An organomolybdenum composition comprising the reaction products of (i) at least one fatty oil; (ii) at least one mono-alkylated alkylene diamine; and (iii) a molybdenum source,
wherein the molar ratio of molybdenum source to mono-alkylated alkylene diamine is from about 2:3 to about 1.15:1.

41. An organomolybdenum composition comprising the reaction products of (i) at least one fatty oil; (ii) at least one mono-alkylated alkylene diamine; and (iii) a molybdenum source, wherein the total base number (TBN) as determined by ASTM D2896 is less than 50 mg KOH/gram.

42. An organomolybdenum composition comprising the reaction products of (i) at least one fatty oil; (ii) at least one mono-alkylated alkylene diamine; and (iii) a molybdenum source, wherein the molar ratio of molybdenum source to mono-alkylated alkylene diamine is from about 2:3 to about 1.15:1, and wherein the total base number (TBN) as determined by ASTM D2896 is less than 50 mg KOH/gram.

43. A process for preparing a molybdenum-containing composition comprising:

(a) combining a material selected from the group consisting of a fatty oil, vegetable oil, a triglyceride, and glycerol ester of a fatty acid, with a mono-substituted alkylene diamine to produce an aminoamide/glycerol carboxylate mixture; and (b) combining the mixture from (a) with a molybdenum source in the presence of water.

44. A product produced by the process of claim 43.

* * * * *